(12) United States Patent
Lee et al.

(10) Patent No.: US 9,095,647 B2
(45) Date of Patent: Aug. 4, 2015

(54) DISPOSABLE STERILIZED CUPPING THERAPY APPARATUS

(75) Inventors: SangHun Lee, Daejeon (KR); Sun-Mi Choi, Daejeon (KR); HeeJung Kang, Ansan-si (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 13/377,874

(22) PCT Filed: Apr. 9, 2010

(86) PCT No.: PCT/KR2010/002198
§ 371 (c)(1),
(2), (4) Date: Dec. 13, 2011

(87) PCT Pub. No.: WO2011/019131
PCT Pub. Date: Feb. 17, 2011

(65) Prior Publication Data
US 2012/0089066 A1   Apr. 12, 2012

(30) Foreign Application Priority Data
Aug. 11, 2009   (KR) .................. 10-2009-0073678

(51) Int. Cl.
*A61F 5/37*    (2006.01)
*A61F 13/00*   (2006.01)
(Continued)

(52) U.S. Cl.
CPC ................. *A61M 1/08* (2013.01); *A61F 13/00* (2013.01); *A61F 13/14* (2013.01); *A61F 13/141* (2013.01);
(Continued)

(58) Field of Classification Search
CPC . A61F 13/00; A61F 13/0051; A61F 13/0068; A61F 13/0089; A61F 2013/0028; A61F 13/14; A61F 13/141; A61F 13/15; A61F 2013/8494; A61F 15/00; A61F 15/004; A61F 15/005; A61F 15/008; A61M 1/00; A61M 1/001; A61M 1/0023; A61M 27/00; A61H 1/00; A61H 1/008; A61H 7/00; A61H 9/00; A61H 9/005; A61H 9/0057
USPC ......... 128/846, 888–894, 842, 844, 869, 917, 128/918; 602/41, 42–44, 53, 56, 79; 601/1, 601/6, 11; 600/37–38; 606/131, 201; 604/19, 27, 35, 39, 48, 73–76, 514
See application file for complete search history.

(56) References Cited

U.S. PATENT DOCUMENTS

| 7,183,454 B1 * | 2/2007 | Rosenberg ...................... 602/43 |
| 7,921,851 B2 * | 4/2011 | Kurz et al. ..................... 128/889 |

(Continued)

FOREIGN PATENT DOCUMENTS

| KR | 20-0264423 | 1/2002 |
| KR | 20-0362549 | 9/2004 |

(Continued)

OTHER PUBLICATIONS
PCT International Search Report for PCT/KR2010/002198.

*Primary Examiner* — Alireza Nia
*Assistant Examiner* — Brandon L Jackson
(74) *Attorney, Agent, or Firm* — Lucas & Mercanti, LLP (57) ABSTRACT

According to the present invention, a disposable sterilized cupping therapy apparatus contains: an expansion part composed of a foldable material, the inner volume of which corresponds to the inner volume of a cupping therapy device when expanded; and a resilient coupling part configured on a perimeter of the expansion part, in which the expansion part is arranged within the cupping therapy device, the coupling part is resiliently pressed against and coupled to a bottom of the cupping therapy device, and the skin of a person receiving therapy that is within the cupping therapy device is sealed from the air outside the expansion part by means of the latter.

15 Claims, 6 Drawing Sheets

(51) Int. Cl.
*A61F 15/00* (2006.01)
*A61N 1/30* (2006.01)
*A61M 1/00* (2006.01)
*A61M 3/02* (2006.01)
*A61M 1/06* (2006.01)
*A61M 31/00* (2006.01)
*A61B 17/50* (2006.01)
*A61B 17/00* (2006.01)
*A61M 1/08* (2006.01)
*A61H 9/00* (2006.01)
*A61H 1/00* (2006.01)
*A61F 13/14* (2006.01)
*A61F 13/15* (2006.01)
*A61M 27/00* (2006.01)
*A61H 7/00* (2006.01)
*A61F 6/02* (2006.01)
*A61F 6/04* (2006.01)

(52) U.S. Cl.
CPC ............... *A61F 13/15* (2013.01); *A61F 15/00* (2013.01); *A61F 15/004* (2013.01); *A61F 15/008* (2013.01); *A61H 1/00* (2013.01); *A61H 1/008* (2013.01); *A61H 7/00* (2013.01); *A61H 9/00* (2013.01); *A61H 9/005* (2013.01); *A61H 9/0057* (2013.01); *A61M 1/00* (2013.01); *A61M 1/0001* (2013.01); *A61M 1/009* (2014.02); *A61M 1/0023* (2013.01); *A61M 27/00* (2013.01)

(56) References Cited

U.S. PATENT DOCUMENTS

| | | | | |
|---|---|---|---|---|
| 8,100,848 B2* | 1/2012 | Wilkes et al. | ............... | 602/61 |
| 2004/0176659 A1* | 9/2004 | Peng et al. | ............... | 600/37 |
| 2005/0267386 A1* | 12/2005 | Copelan | ............... | 601/14 |

FOREIGN PATENT DOCUMENTS

| | | |
|---|---|---|
| KR | 10-0470808 | 1/2005 |
| KR | 20-0441651 | 8/2008 |
| KR | 20-2009-0004791 | 5/2009 |
| KR | 10-2009-0078010 | 7/2009 |

* cited by examiner

DISPOSABLE STERILIZED CUPPING THERAPY APPARATUS

CROSS-REFERENCE TO RELATED APPLICATIONS

This application is a 371 of PCT/KR2010/002198, filed Apr. 9, 2010, which claims the benefit of Korean Patent Application No. 10-2009-0073678, filed Aug. 11, 2009, the contents of each of which are incorporated herein by reference.

TECHNICAL FIELD

The present invention relates, in general, to a disposable sterilized cupping therapy apparatus and, more particularly, to a disposable sterilized cupping therapy apparatus which is capable of preventing bacterial infection caused by indirect contact with a suction part, in addition to reducing the volume required to store the apparatus.

BACKGROUND ART

A conventional disposable cupping therapy unit or cupping cap has an evacuation hole in an upper end thereof to generate negative pressure. Such a configuration inevitably leads to a small amount of air flow between a suction part and the cupping therapy unit.

Generally, the suction part for creating negative pressure is not disposable but is used several times repeatedly. Hence, there is a great danger of bacteria propagating.

Thus, if the passage between the suction part and the skin of a person who receives therapy is not blocked, his or her skin may become infected. The wet cupping therapy which damages the skin is especially affected by the above hygienic problem.

Meanwhile, since the disposable cupping therapy unit or cupping cap is made of a hard plastic material which can withstand the negative pressure, it occupies a large space when stored or carried, the manufacturing cost is high, and in addition a large space is required when it is disposed of. Further, the disposable cupping therapy unit is not individually packaged, so that it is difficult to store the disposable cupping therapy unit in a perfectly sanitary manner.

DISCLOSURE

Technical Problem

Accordingly, the present invention has been made keeping in mind the above problems occurring in the prior art, and an object of the present invention is to provide a disposable sterilized cupping therapy apparatus, which prevents a bacterial infection caused by indirect contact with a suction part, enables perfect sanitation using individual sterilized packaging, and reduces the volume required for storage.

Technical Solution

In order to accomplish the above object, the present invention provides a disposable sterilized cupping therapy apparatus, including an expansion part 20 made of a foldable material, a volume thereof corresponding to an inner volume of a cupping therapy unit 2 when expanded; and a resilient coupling part 40 provided on a perimeter of the expansion part 20, wherein the expansion part 20 is disposed in the cupping therapy unit 2, and the coupling part 40 is resiliently pressed against and coupled to a bottom of the cupping therapy unit 2, so that the expansion part 20 isolates a skin 1 of a therapy receiving person that is inside the cupping therapy unit 2 from the air outside the expansion part 20.

The coupling of the coupling part 40 to the bottom of the cupping therapy unit 2 by means of resilient pressing may be performed by outwardly stretching the coupling part 40 through the bottom of the cupping therapy unit 2 to press an outer surface of the bottom of the cupping therapy unit 2 inwards, after placing the coupling part 40 and the expansion part 20 inside the cupping therapy unit 2.

Preferably, the expansion part 20 and the coupling part 40 may be integrated into a single structure and may be made of a vinyl material.

The apparatus may further include gauze 60 attached to a surface of the expansion part 20 facing the person's skin 1 to absorb extravasated blood oozing from a wound of the person's skin 1.

Advantageous Effects

According to the present invention, a disposable sterilized cupping therapy apparatus is advantageous in that an expansion part isolates a person's skin located in a cupping therapy unit from the air outside the expansion part during cupping therapy, thus preventing air flow between his or her skin and a suction part in which bacteria are easily propagated when it is used several times, and thereby preventing bacterial infection.

Further, a disposable sterilized cupping therapy apparatus is advantageous in that gauze attached to an expansion part absorbs extravasated blood oozing from the wound of a person's skin, thus removing the blood in a sanitary way.

Furthermore, a disposable sterilized cupping therapy apparatus is advantageous in that the external volume that it occupies is considerably less than that of a conventional disposable cupping therapy unit or cupping cap, thus allowing the apparatus to be efficiently stored or carried.

DESCRIPTION OF REFERENCE CHARACTERS OF IMPORTANT PARTS

1: skin of person receiving therapy
2: cupping therapy unit
2a: evacuation hole 2b: body 2c: bottom 3: suction part
20: expansion part 40: coupling part
60: gauze

MODE FOR INVENTION

Figure 1:
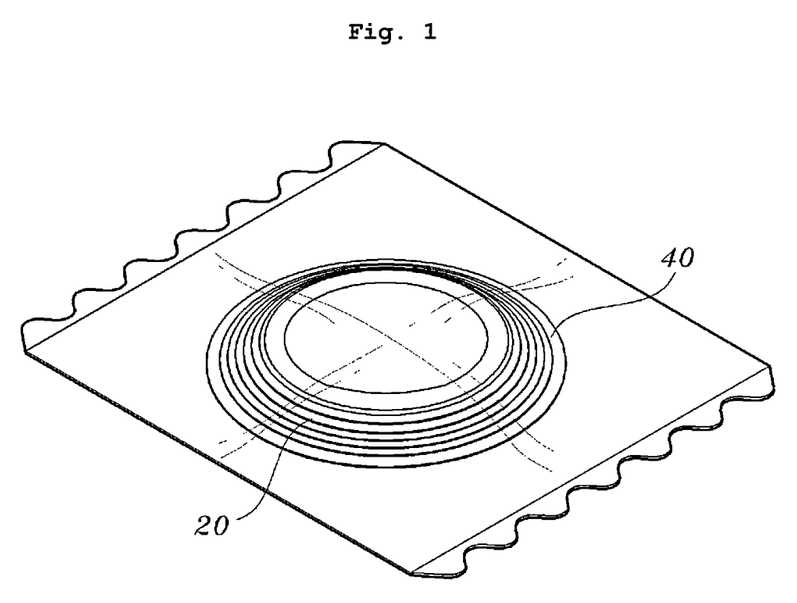
FIG. 1 is a view illustrating a disposable sterilized cupping therapy apparatus in accordance with a preferred embodiment of the present invention, in which it is packaged.
Figure 2:
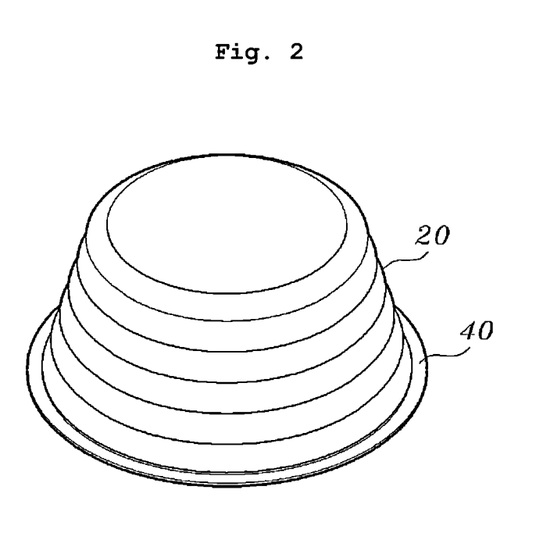
FIG. 2 is a view illustrating the disposable sterilized cupping therapy apparatus of FIG. 1.

FIG. 1 is a view illustrating a disposable sterilized cupping therapy apparatus in accordance with a preferred embodiment of the present invention, in which it is packaged, and FIG. 2 is a view illustrating the disposable sterilized cupping therapy apparatus of FIG. 1.

Referring to the drawings, the apparatus of the present invention includes an expansion part 20 made of a foldable material, and a coupling part 40 provided on a perimeter of the expansion part 20.

The expansion part 20 is made of the foldable material. That is, it is not hard so as to have a fixed appearance, but may be able to be folded and be collapsible.

Of course, the expansion part 20 may be made of a flexible material. The flexible material allows the expansion part 20 to be easily deformed into a shape that reduces the volume like a folded shape, in addition to maintaining such a deformed shape.

Further, the coupling part 40 is provided on the perimeter of the expansion part 20 while retaining resilience.

That is, the coupling part placed along the perimeter of the expansion part 20 has resilience to return to its original state after it has been stretched.

Preferably, the expansion part 20 and the coupling part 40 configured as such are integrated with each other, and are made of a vinyl material. The expansion part 20 and the coupling part 40 are naturally limited to the material of the present invention. Any material may be used as long as it has the above-mentioned characteristics.

Thus, the volume of the apparatus according to the present invention is very small so that it occupies a small amount of space, thus enabling its efficient storage or transportation.

Moreover, the present invention allows cupping therapy to be performed at a low cost in a sanitary and convenient way.

Figure 3:
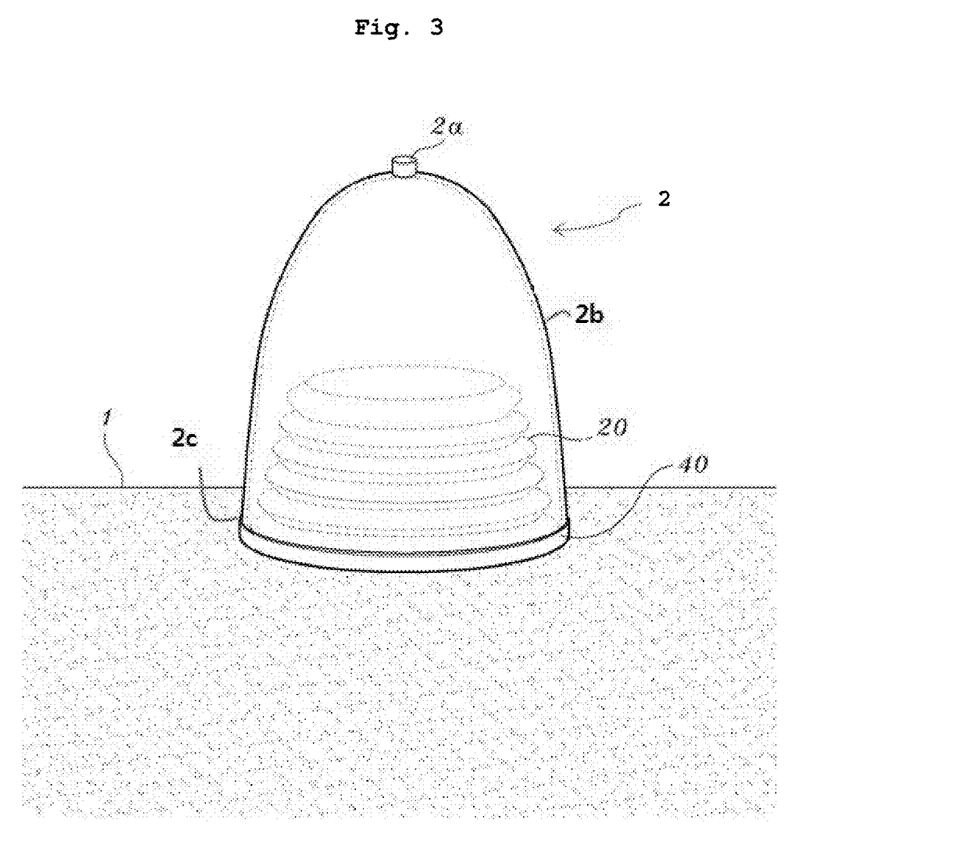
FIG. 3 is a view illustrating the disposable sterilized cupping therapy apparatus of FIG. 1, in which it is coupled to a cupping therapy unit.

Meanwhile, FIG. 3 is a view illustrating the disposable sterilized cupping therapy apparatus of FIG. 1, in which it is coupled to a cupping therapy unit 2.

Referring to the drawing, when the coupling part 40 is used together with the cupping therapy unit 2 for cupping therapy, the coupling part 40 and the expansion part 20 are located in a body 2b of the cupping therapy unit 2, and the coupling part 40 is resiliently pressed against and coupled to a bottom 2c of the cupping therapy unit 2.

That is, the coupling part 40 has a diameter smaller than that of the bottom of the cupping therapy unit 2. Hence, while the coupling part 40 located in the cupping therapy unit 2 extends outwards through the bottom of the cupping therapy unit 2, the coupling part inwardly presses an outer surface of the bottom of the cupping therapy unit 2.

After a therapy conducting person stretches the coupling part 40 to an outer portion of the cupping therapy unit 2 and pulls the coupling part upwards by a predetermined distance, the coupling part 40 is released. At this time, the coupling part 40 adheres to the outer surface of the bottom of the cupping therapy unit 2, and pushes the bottom of the cupping therapy unit 2 inwards with a strong force, thus maintaining a fixed state.

In such a state, the expansion part 20 isolates the person's skin 1 located in the cupping therapy unit 2 from the air outside the expansion part 20.

Figure 4:
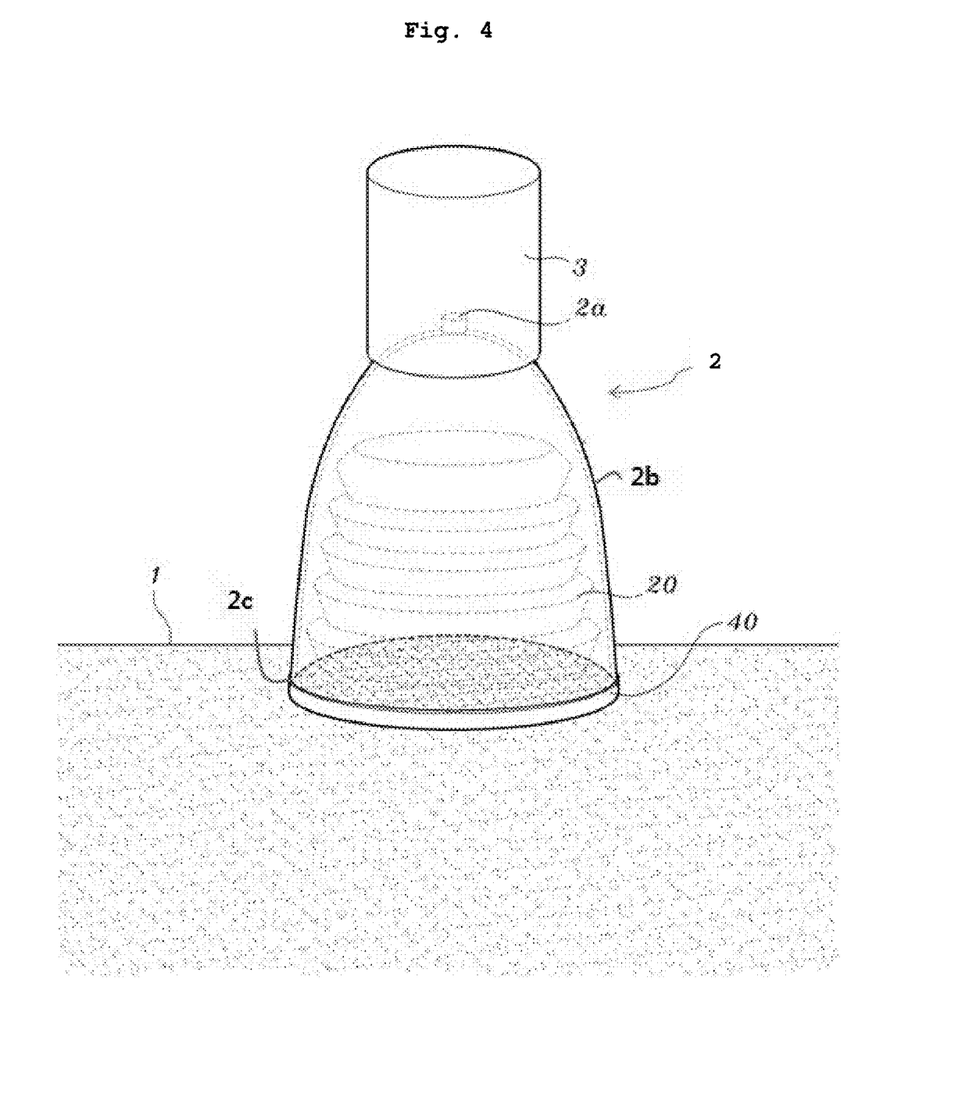
FIG. 4 is a view illustrating the disposable sterilized cupping therapy apparatus of FIG. 1, in which an expansion part of the apparatus is expanded in the cupping therapy unit by a suction part.

The use of the disposable sterilized cupping therapy apparatus according to the preferred embodiment configured as described above, together with the cupping therapy unit 2, will be described with reference to FIG. 4.

First, the disposable sterilized cupping therapy apparatus composed of the expansion part 20 and the coupling part 40 is placed in the cupping therapy unit 2. Next, the coupling part 40 provided on the perimeter of the expansion part 20 is stretched and is resiliently pressed against the outer surface of the bottom of the cupping therapy unit 2, thus firmly coupling the disposable sterilized cupping therapy apparatus to the cupping therapy unit 2.

Subsequently, the cupping therapy unit 2 coupled with the disposable sterilized cupping therapy apparatus is placed on the person's skin 1 which is to be treated. Air pressure in the cupping therapy unit 2 is reduced by cooperation between the suction part 3 and an evacuation hole 2a (see FIG. 3) formed in an upper end of the body 2b of the cupping therapy unit 2, thus creating negative pressure in the cupping therapy unit.

During such a process, the expansion part 20 is expanded upwards by the negative pressure in the cupping therapy unit 2, so that the negative pressure achieves a uniform state in the cupping therapy unit 2.

Here, if the expansion part 20 does not expand, a strong negative pressure in the cupping therapy unit 2 is created only outside the expansion part 20, and little negative pressure is created in the expansion part 20, so that the cupping therapy is not applied to the person's skin 1 located in the expansion part 20.

Consequently, in the cupping therapy according to the present invention, the expansion part 20 isolates the person's skin 1 located in the cupping therapy unit 2 from the air outside the expansion part 20.

Thereby, air flow is interrupted between the skin 1 of the person who is receiving the cupping therapy and the suction part 3 in which bacteria are easily propagated when it is used several times, thus preventing the person from being infected with the bacteria of the suction part 3 through the evacuation hole 2a.

Further, this invention is advantageous because it can prevent infection by bacteria existing in the cupping therapy unit 2, in addition to keeping the apparatus more sanitary by providing completely sterilized packaging.

Moreover, when it is required to manage the apparatus in a more sanitary manner, for example, in the case of wet cupping therapy which damages the skin 1, the present invention achieves a high sanitary effect.

That is, the present invention can effectively prevent a wound that bleeds during wet cupping therapy from being infected with the bacteria.

Figure 5:
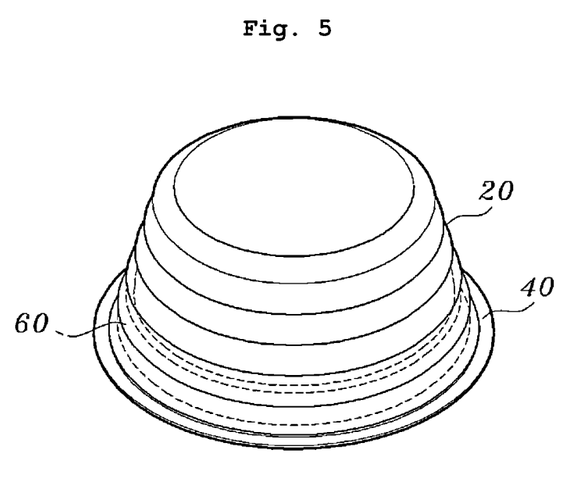
FIG. 5 is a view illustrating a disposable sterilized cupping therapy apparatus in accordance with another preferred embodiment of the present invention.
Figure 6:
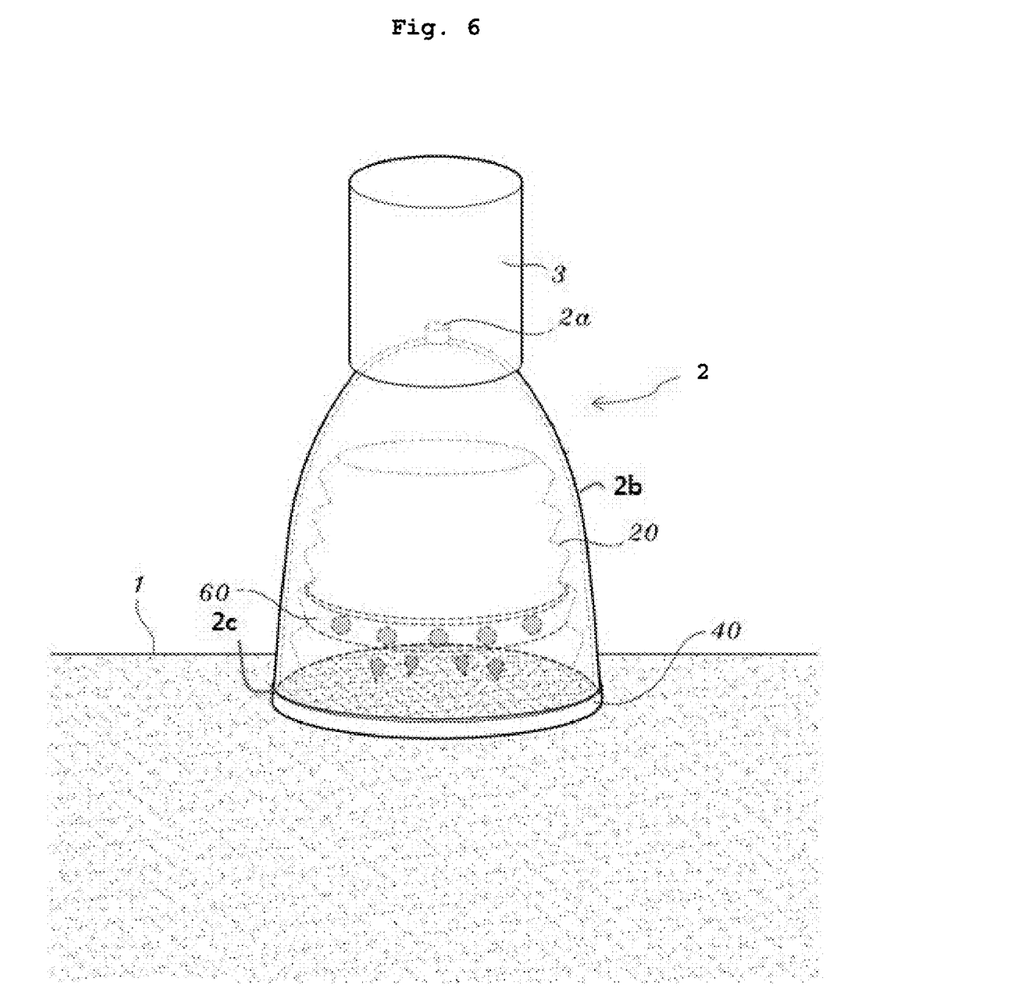
FIG. 6 is a view illustrating the disposable sterilized cupping therapy apparatus of FIG. 5, in which an expansion part of the apparatus is expanded in the cupping therapy unit by the suction part.

FIG. 5 is a view illustrating a disposable sterilized cupping therapy apparatus in accordance with another preferred embodiment of the present invention, and FIG. 6 is a view illustrating the disposable sterilized cupping therapy apparatus of FIG. 5, in which an expansion part of the apparatus is expanded in the cupping therapy unit by the suction part.

Referring to the drawings, the disposable sterilized cupping therapy apparatus may further include gauze 60 attached to a surface of the expansion part 20 facing the person's skin 1 so as to absorb extravasated blood generated by the skin 1.

The gauze 60 absorbs blood oozing from the wound of the skin 1, thus removing the blood in a sanitary way. It is preferable to use the sterilized gauze 60.

Here, as long as the gauze 60 is located at a position of the expansion part 20 from which blood can be smoothly absorbed, the position and the method of attaching the gauze are not limited to the embodiment of the present invention.

As a result, the present invention can prevent bacterial infection caused by indirect contact with the suction part 3, and can reduce the volume required for storage.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A disposable sterilized cupping therapy apparatus in a cupping therapy unit, comprising:
an expansion part made of a foldable material, a volume thereof corresponding to an inner volume of a cupping therapy unit when expanded; and
a resilient coupling part provided on a perimeter of the expansion part,
wherein the expansion part and the coupling part are integrated into a single structure,
wherein the cupping therapy unit comprises:
a body having an inner hollow space corresponding to said inner volume, the hollow space being configured to receive the expansion part of the disposable sterilized cupping therapy apparatus when expanded;
a bottom to be contacted on a skin of a person to receive a cupping therapy through a portion of the resilient coupling part; and
an evacuation hole,
wherein the cupping therapy unit is configured to be coupled to the disposable sterilized cupping therapy apparatus during the cupping therapy,
wherein the expansion part is disposed inside the cupping therapy unit, and the coupling part is exposed outside the cupping therapy unit to press an outer surface of a bottom of the cupping therapy unit inwards, so that the expansion part isolates a skin of a therapy receiving person that is inside the cupping therapy unit from air outside the expansion part, and
wherein the coupling part before being coupled to the cupping therapy unit has a diameter smaller than that of the bottom of the cupping therapy unit to inwardly press an outer surface of the bottom of the cupping therapy unit when the coupling part extends outwards through the bottom of the cupping therapy unit.

2. The disposable sterilized cupping therapy apparatus according to claim 1, wherein the expansion part and the coupling part are made of a vinyl material.

3. The disposable sterilized cupping therapy apparatus according to claim 1, further comprising:
gauze attached to a surface of the expansion part facing the person's skin to absorb extravasated blood oozing from a wound of the person's skin.

4. The disposable sterilized cupping therapy apparatus according to claim 1, wherein the expansion part comprises a plurality of folds in an expanded state.

5. A disposable sterilized cupping therapy apparatus in a cupping therapy unit, comprising:
an expansion part made of a flexible material adapted with a plurality of folds, the folds allowing a transition between a collapsed state and an expanded state whereby the expansion part in the expanded state provides an interior volume; and
a resilient coupling part made of flexible material provided on a perimeter of the expansion part,
wherein the expansion part and the coupling part are integrated into a single structure,
wherein the cupping therapy unit comprises:
a body having a inner hollow space corresponding to said inner volume, the hollow space being configured to receive the expansion part of the disposable sterilized cupping therapy apparatus when expanded;
a bottom to be contacted on a skin of a person to receive a cupping therapy through a portion of the resilient coupling part, and
an evacuation hole,
wherein the cupping therapy unit is configured to be coupled to the disposable sterilized cupping therapy apparatus during the cupping therapy, and
wherein the expansion part is disposed inside the cupping therapy unit, and the coupling part is exposed outside the cupping therapy unit, thereby resiliently pressing an outer surface of a bottom of the cupping therapy unit inwards, so that the expansion part isolates a skin of a therapy receiving person that is inside the cupping therapy unit from air outside the expansion part.

6. The disposable sterilized cupping therapy apparatus according to claim 5, wherein the folds are in a concentric pattern.

7. The disposable sterilized cupping therapy apparatus according to claim 5, wherein the coupling part before being coupled to the cupping therapy unit has a diameter smaller than that of the bottom of the cupping therapy unit to inwardly press an outer surface of the bottom of the cupping therapy unit when the coupling part extends outwards through the bottom of the cupping therapy unit.

8. The disposable sterilized cupping therapy apparatus according to claim 5, wherein the expansion part and the coupling part are made of a vinyl material.

9. The disposable sterilized cupping therapy apparatus according to claim 5, further comprising: gauze attached to a surface of the expansion part facing the person's skin to absorb extravasated blood oozing from a wound of the person's skin.

10. The disposable sterilized cupping therapy apparatus according to claim 5, wherein the expansion part comprises the folds in the expanded state.

11. A cupping therapy apparatus comprising
a disposable sterilized cupping therapy apparatus, and
a cupping therapy unit configured to be coupled to the disposable sterilized cupping therapy apparatus during cupping therapy,
wherein the disposable sterilized cupping therapy apparatus comprises:
an expansion part made of a foldable material,
a volume thereof corresponding to an inner volume of the cupping therapy unit when expanded; and
a resilient coupling part provided on a perimeter of the expansion part,
wherein the expansion part and the coupling part are integrated into a single structure,
wherein the cupping therapy unit comprises:
a body having a inner hollow space corresponding to said inner volume, the hollow space being configured to receive the expansion part of the disposable sterilized cupping therapy apparatus when expanded;
a bottom to be contacted on a skin of a person to receive a cupping therapy unit through a portion of the resilient coupling part, and
an evacuation hole,
wherein the expansion part is disposed inside the cupping therapy unit, and the coupling part is exposed outside the cupping therapy unit to press an outer surface of a bottom of the cupping therapy unit inwards so that the expansion part isolates a skin of a therapy receiving person that is inside the cupping therapy unit from air outside the expansion part, and wherein the coupling part before being coupled to the cupping therapy unit has a diameter smaller than that of the bottom of the cupping therapy unit to inwardly press an outer surface of the bottom of the cupping therapy unit when the coupling part extends outwards through the bottom of the cupping therapy unit.

12. The disposable sterilized cupping therapy apparatus according to claim 11, wherein the expansion part and the coupling part are made of a vinyl material.

13. The disposable sterilized cupping therapy apparatus according to claim 11, further comprising: gauze attached to a surface of the expansion part facing the person's skin to absorb extravasated blood oozing from a wound of the person's skin.

14. The disposable sterilized cupping therapy apparatus according to claim 11, wherein an expansion part made of a foldable material adapted with a plurality of folds, the folds allowing a transition between a collapsed state and an expanded state whereby the expansion part in the expanded state provides an interior volume.

15. The disposable sterilized cupping therapy apparatus according to claim 11, wherein the expansion part comprises a plurality of folds in an expanded state.

\* \* \* \* \*